(12) United States Patent
Han et al.

(10) Patent No.: US 9,095,831 B2
(45) Date of Patent: Aug. 4, 2015

(54) FLUID BED REACTOR WITH STAGED BAFFLES

(75) Inventors: Lu Han, Herndon, VA (US); Rathna P. Davuluri, Fairfax, VA (US); Christopher G. Smalley, Manassas, VA (US); Mark P. Hagemeister, Houston, TX (US); Masaaki Sugita, McLean, VA (US); Joseph S. Famolaro, Ashburn, VA (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 351 days.

(21) Appl. No.: 13/557,605

(22) Filed: Jul. 25, 2012

(65) Prior Publication Data
US 2013/0165724 A1 Jun. 27, 2013

Related U.S. Application Data

(60) Provisional application No. 61/512,271, filed on Jul. 27, 2011.

(51) Int. Cl.
| | |
|---|---|
| *B01J 8/18* | (2006.01) |
| *B01J 8/34* | (2006.01) |
| *C07C 2/86* | (2006.01) |
| *B01J 8/00* | (2006.01) |
| *B01J 8/24* | (2006.01) |
| *B01J 19/32* | (2006.01) |

(Continued)

(52) U.S. Cl.
CPC *B01J 8/34* (2013.01); *B01J 8/1818* (2013.01); *B01J 8/1827* (2013.01); *B01J 8/1872* (2013.01); *C07C 2/864* (2013.01); *C07C 2/865* (2013.01)

(58) Field of Classification Search
CPC .................. B01J 8/00; B01J 8/08; B01J 8/12; B01J 8/125; B01J 8/18; B01J 8/1845; B01J 8/1872; B01J 8/1881; B01J 8/24; B01J 8/26; B01J 8/28; B01J 8/34; B01J 8/44; B01J 19/00; B01J 19/24; B01J 19/30; B01J 19/305; B01J 19/32; B01J 19/325; B01J 20/30; B01J 20/3092; B01J 2219/00; B01J 2219/30; B01J 2219/302; B01J 2219/33; C07C 2/54; C07C 2/56; C07C 2/58; C07C 2/64; C07C 2/66; C07C 15/00; C07C 15/02; C07C 15/04; C07C 15/06; C07C 15/067; C07C 15/073; C07C 15/08
USPC ......... 422/129, 139, 141, 142, 187, 600, 630, 422/631, 633, 635, 642, 644
See application file for complete search history.

(56) References Cited

U.S. PATENT DOCUMENTS 3,849,291 A * 11/1974 Owen .............................. 208/78
3,982,903 A 9/1976 Anderson
(Continued)

FOREIGN PATENT DOCUMENTS

GB 803 458 10/1958

*Primary Examiner* — Natasha Young

(57) ABSTRACT

The invention relates to a process of alkylating aromatic hydrocarbons, and more particularly a process of making paraxylene by alkylation of benzene and/or toluene with methanol and/or dimethyl ether, and to an apparatus for carrying out said process, the improvement comprising staged injection of one of the reactants, with the stages separated by structured packing so as to minimize at least one of gas phase back-mixing, by-pass phenomena, and gas bubble size.

10 Claims, 3 Drawing Sheets

(51) Int. Cl.

| | | |
|---|---|---|
| C07C 2/54 | (2006.01) | |
| C07C 2/56 | (2006.01) | |
| C07C 2/58 | (2006.01) | |
| C07C 2/64 | (2006.01) | |
| C07C 2/66 | (2006.01) | |
| C07C 15/00 | (2006.01) | |
| C07C 15/02 | (2006.01) | |
| C07C 15/04 | (2006.01) | |
| C07C 15/06 | (2006.01) | |
| C07C 15/08 | (2006.01) | |

(56) References Cited

U.S. PATENT DOCUMENTS

| | | |
|---|---|---|
| 4,002,698 A | 1/1977 | Kaeding |
| 4,197,418 A * | 4/1980 | Lee et al. ............... 585/469 |
| 4,251,484 A | 2/1981 | Daviduk et al. |
| 4,313,848 A * | 2/1982 | Scott ............... 502/47 |
| 4,356,338 A | 10/1982 | Young |
| 4,423,266 A | 12/1983 | Young |
| 4,855,111 A | 8/1989 | Bader et al. |
| 5,675,047 A | 10/1997 | Beck et al. |
| 5,804,690 A | 9/1998 | Chang et al. |
| 5,939,597 A | 8/1999 | Dessau et al. |
| 6,028,238 A | 2/2000 | Beck et al. |
| 6,046,372 A | 4/2000 | Brown et al. |
| 6,048,816 A | 4/2000 | Brown et al. |
| 6,156,949 A | 12/2000 | Brown et al. |
| 6,423,879 B1 | 7/2002 | Brown et al. |
| 6,504,072 B1 | 1/2003 | Brown et al. |
| 6,506,954 B1 | 1/2003 | Brown et al. |
| 6,538,167 B1 | 3/2003 | Brown et al. |
| 6,642,426 B1 | 11/2003 | Johnson et al. |
| 6,897,346 B1 | 5/2005 | Merrill et al. |
| 7,232,936 B1 * | 6/2007 | Yurchak ............... 585/640 |
| 7,935,857 B2 | 5/2011 | Beech et al. |
| 2009/0269252 A1 * | 10/2009 | Yuan et al. ............... 422/145 |
| 2011/0319692 A1 * | 12/2011 | Spieker et al. ............... 585/659 |

* cited by examiner

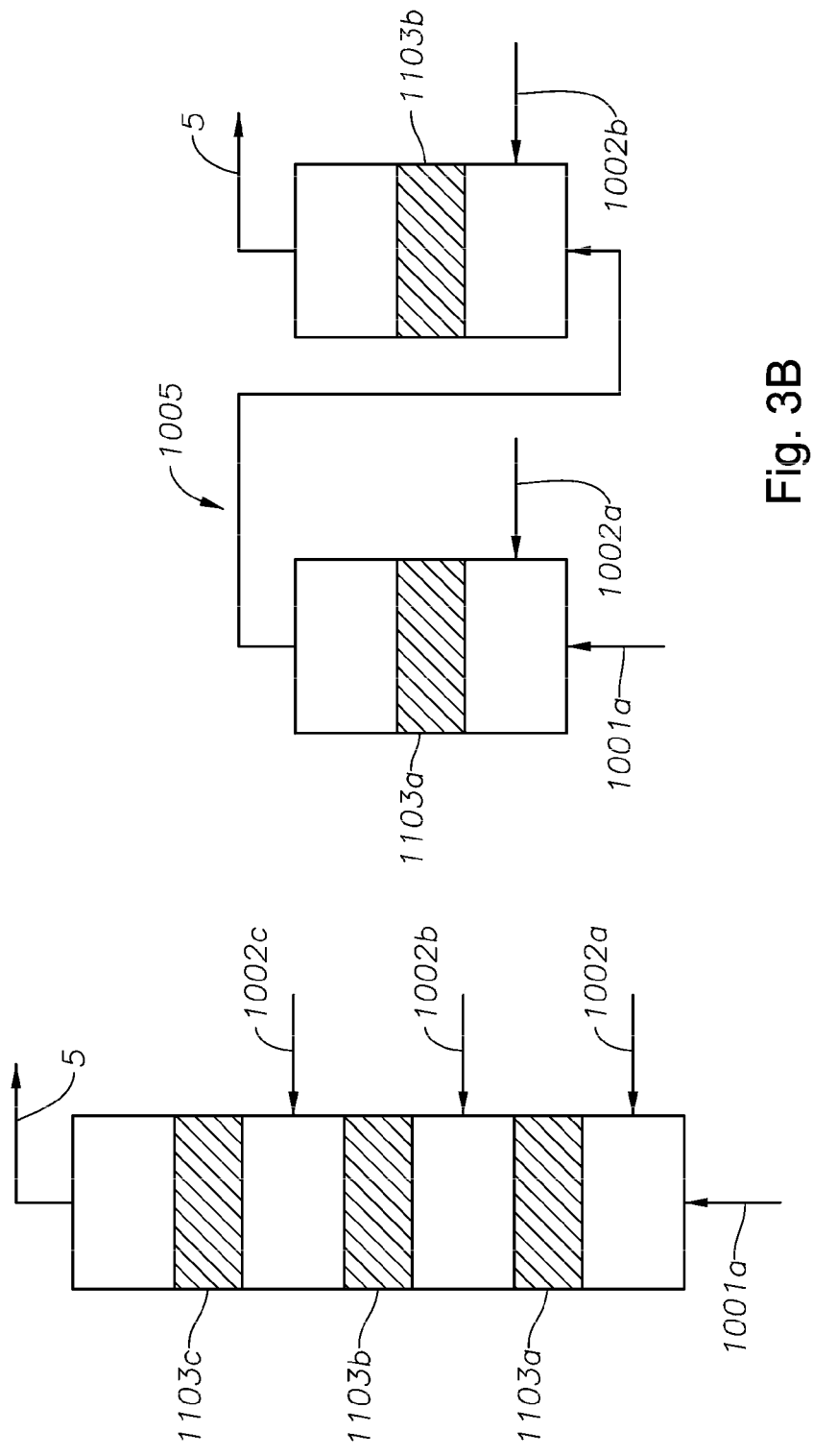

FLUID BED REACTOR WITH STAGED BAFFLES

PRIORITY CLAIM

This application claims the benefit of Provisional Application No. 61/512,271, filed Jul. 27, 2011, the disclosure of which is incorporated by reference in its entirety.

FIELD OF THE INVENTION

The invention relates to a process of alkylating aromatic hydrocarbons, and more particularly a process of making paraxylene by alkylation of benzene and/or toluene with methanol, and to an apparatus for carrying out said process.

BACKGROUND OF THE INVENTION

It is well-known to manufacture xylenes by the alkylation of toluene and/or benzene with methanol, and in particular to selectively make paraxylene (PX) product using zeolite catalyst. See, for instance, U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426. The terms "paraxylene selectivity", "para-selective", and the like, means that paraxylene is produced in amounts greater than is present in a mixture of xylene isomers at thermodynamic equilibrium, which at ordinary processing temperatures is about 24 mol %. Paraxylene selectivity is highly sought after because of the economic importance of paraxylene relative to meta- and orthoxylene. Although each of the xylene isomers have important and well-known end uses, paraxylene is currently the most economically valuable, serving as an intermediate in such important and diverse end uses as bottle plastic and polyester fibers.

In the process, typically toluene and/or benzene are alkylated with methanol, in the presence of a suitable catalyst, to form xylenes in a reactor in a system illustrated schematically in FIG. 1, wherein a feed comprising reactants enter fluid bed reactor 11 via conduit 1 and effluent comprising product exits through conduit 5, and the catalyst circulates between fluid bed reactor 11, apparatus 12, which strips fluid from the catalyst, and catalyst regenerator 13, via conduits 2, 3, and 4, respectively. Water is typically co-fed with toluene and methanol to minimize toluene coking in the feed lines and methanol self-decomposition. Other side reactions include the formation of light olefins, light parafins, as reactions that convert paraxylenes to other xylene isomers or heavier aromatics.

Apparatus suitable for each of the elements shown in FIG. 1 are per se well-known in the art, however as one of ordinary skill in the art will recognize simply picking and choosing for what is available will not arrive at a commercially viable system. There are numerous problems to overcome, and arriving at a system which can compete with other known methods of making paraxylene selectively, such as transalkylation and toluene disproportionation, is the subject of intense current research in the industry. A few of the problems are outlined below.

Gas bubbles formed at the bottom of a fluid bed will grow as they rise through the bed until they reach a maximum stable bubble size. Because the bubbles will grow at different rates, there will be typically a broad distribution of bubble sizes in a fluidized bed. A broad bubble size distribution can cause significant gas phase back-mixing both at a local level due to formation of turbulent eddies as well as at the global level due to uneven axial velocity profiles across the horizontal direction. Such gas back-mixing keeps portions of the desired product in contact with active catalyst for longer than the expected plug flow reactor residence time. On the other hand, while back-mixing increases gas phase residence time, another phenomenon can simultaneously result in decrease of the gas phase residence time. Large bubbles can also form continuous gulf-streaming flow structures which result in gas by-pass, which allows gas to quickly pass through the bed with little contact with catalyst.

Poor contact between gas and active catalyst in the by-pass zone results in reduced reactant conversion and low fluid bed (reactor volume) utilization.

The use of a baffled system is known from U.S. Pat. No. 7,935,857. Other relevant references include U.S. Pat. Nos. 4,251,484; 3,982,903; 4,855,111; 6,642,426; and GB 803458.

While backmixing is generally considered good for methanol conversion, the present inventors have discovered that staged injection in the presence of a baffle system avoids secondary reactions such as isomerization of the desired paraxylene to its less desirable isomers, and improves selectivity to paraxylene from about 60-70 wt % to above 80 wt %, such as to 80-90 wt % in embodiments. Without wishing to be bound by theory, the present inventors have surprisingly discovered a process and apparatus or system adapted therefore, wherein the combination of reduced gas phase back-mixing and by-pass phenomena can work in concert to improve both conversion and selectivity, as well as increase catalyst utilization, by the use of staging baffles in a deep fluid bed to yield smaller and more uniform, and thus controllable, bubble sizes, and combining staged methanol injection to the reactor bed with the use of structured packing layers as staging baffles selectivity to more efficiently provide the desired products.

SUMMARY OF THE INVENTION

The invention is directed to a process of alkylating aromatic hydrocarbons, and more particularly a process of making paraxylene by alkylation of benzene and/or toluene with methanol and/or dimethylether (DME), and to an apparatus for carrying out said process, the improvement comprising the staged injection of at least one of the reactants, benzene and/or toluene and methanol, wherein plural injection stages are separated by baffle material, preferably structured material, so as to decrease at least one of gas phase back-mixing, by-pass phenomena, and gas bubble size.

These and other objects, features, and advantages will become apparent as reference is made to the following detailed description, preferred embodiments, examples, and appended claims.

BRIEF DESCRIPTION OF THE DRAWINGS

A more complete understanding of the present invention and advantages thereof may be acquired by referring to the following description and the accompanying drawings, in which like reference numbers indicate like features.

FIGS. 3A and 3B illustrate schematically embodiments of the reactor system according to the present invention.

DETAILED DESCRIPTION

Figure 1:
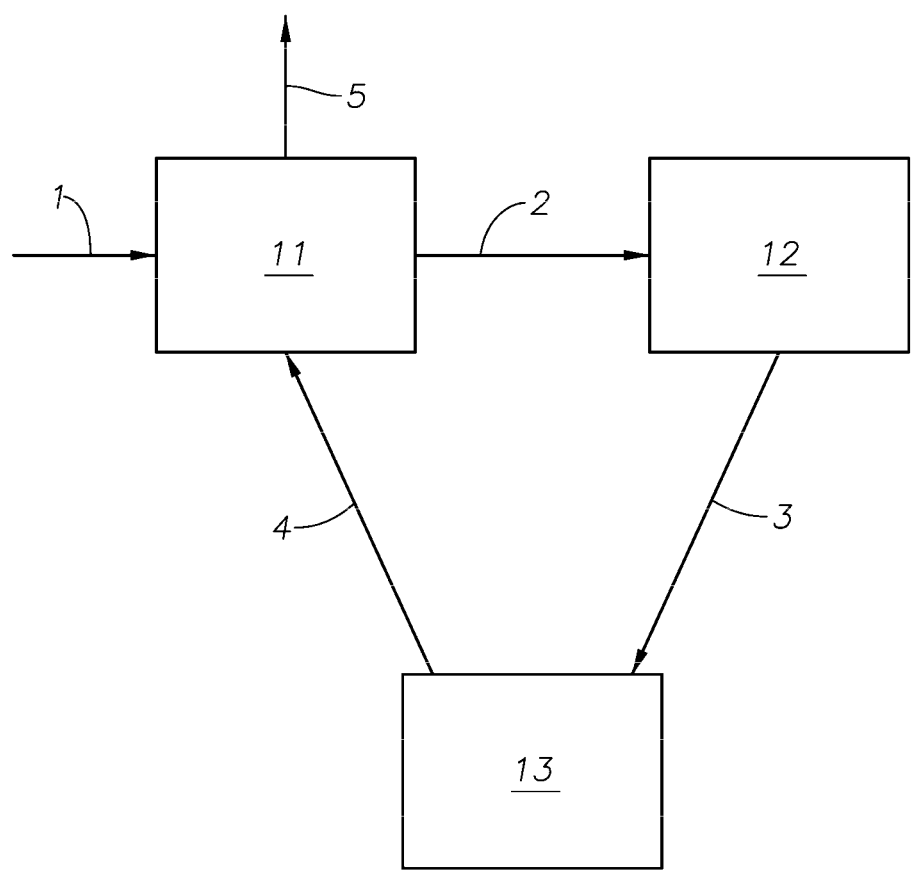
FIG. 1 is a schematic of a reactor system including reactor and regenerator and some associated auxiliary devices and transfer piping per se known in the art.

According to the invention, there is a process for the manufacture of paraxylene selectively by contact of benzene and/or toluene with a catalyst that promotes the selective production of paraxylene from said contact (or "a suitable catalyst") in a fluid bed reactor, the improvement comprising the injection of at least one reactant into said reactor in stages, wherein each stage is separated from the next stage by baffle material, preferably structured packing. In preferred embodiments, there is a fluidized bed process for the alkylation of aromatic hydrocarbons by contact of reactants in the presence of a catalyst that promotes said alkylation, said process characterized by the generation of gas bubbles within a fluid bed reactor system, the improvement comprising the introduction of at least one of said reactants by injection at plural locations within said reactor system, each location defined as a stage spaced apart from at least one other stage, and wherein at least one stage is separated from the at least one other stage by baffle material, such as structured packing so, as to decrease at least one of gas phase back-mixing, by-pass phenomena, and gas bubble size.

The invention is also directed to an apparatus for the manufacture of paraxylene selectively by contact of benzene and/or toluene with a suitable molecular sieve catalyst in a fluid bed reactor, the improvement comprising the injection of at least one reactant into said reactor in stages, wherein each stage is separated from the next stage by baffle material, preferably structured packing. In an alternative, the stages may be in one or more separate reactors in series, wherein at least one of said stages is adjacent to and upstream of baffle material in order to achieve the purpose of the present invention. In preferred embodiments, there is a fluid bed reactor system for the manufacture of xylene by an alkylation reaction comprising contact of an alkylating agent with benzene and/or toluene in the presence of a catalyst that promotes said alkylation reaction, the improvement comprising the staged injection of at least one of the reactants, benzene and/or toluene and methanol and/or dimethylether, wherein plural injection stages are separated by baffle material, such as structured packing, said baffle material characterized as suitable to decrease at least one of gas phase back-mixing, by-pass phenomena, and gas bubble size in the manufacture of xylene by said alkylation reaction. In the discussion below reference will be made to methanol as the alkylating agent, however it will be recognized that dimethyl ether may also be used, alone or in mixture with methanol.

The term "baffle material" as used herein refers to structured and unstructured material, e.g., aggregate or column packing material. The present inventors have found that structured material provides certain additional benefits in the present invention as compared with unstructured material. The term "structured material" is per se well known in the art and can be defined as packing wherein individual members have specific orientation relative to each other and to the column axis. See U.S. Pat. No. 5,132,056.

Without wishing to be bound by theory, the combination of gas phase back-mixing and by-pass reduction phenomena work in concert to improve both conversion and selectivity, as well as increase catalyst utilization, by use of a deep fluid bed design comprising staged methanol injection to minimize methanol side reactions, and structured packing to separate the stages.

Since the desired product is an intermediate in the reaction chains, it is important to control gas back-mixing and gas by-pass which a deep fluid bed is usually prone to. The selectivity for the desired paraxylene product is maximized by reducing gas phase back-mixing with a few layers of structured packing which function as staging baffles in the fluid bed reactor. The staging baffles also have the added beneficial effect of minimizing gas by-pass which, if not controlled, would reduce reactor utilization.

Figure 2:
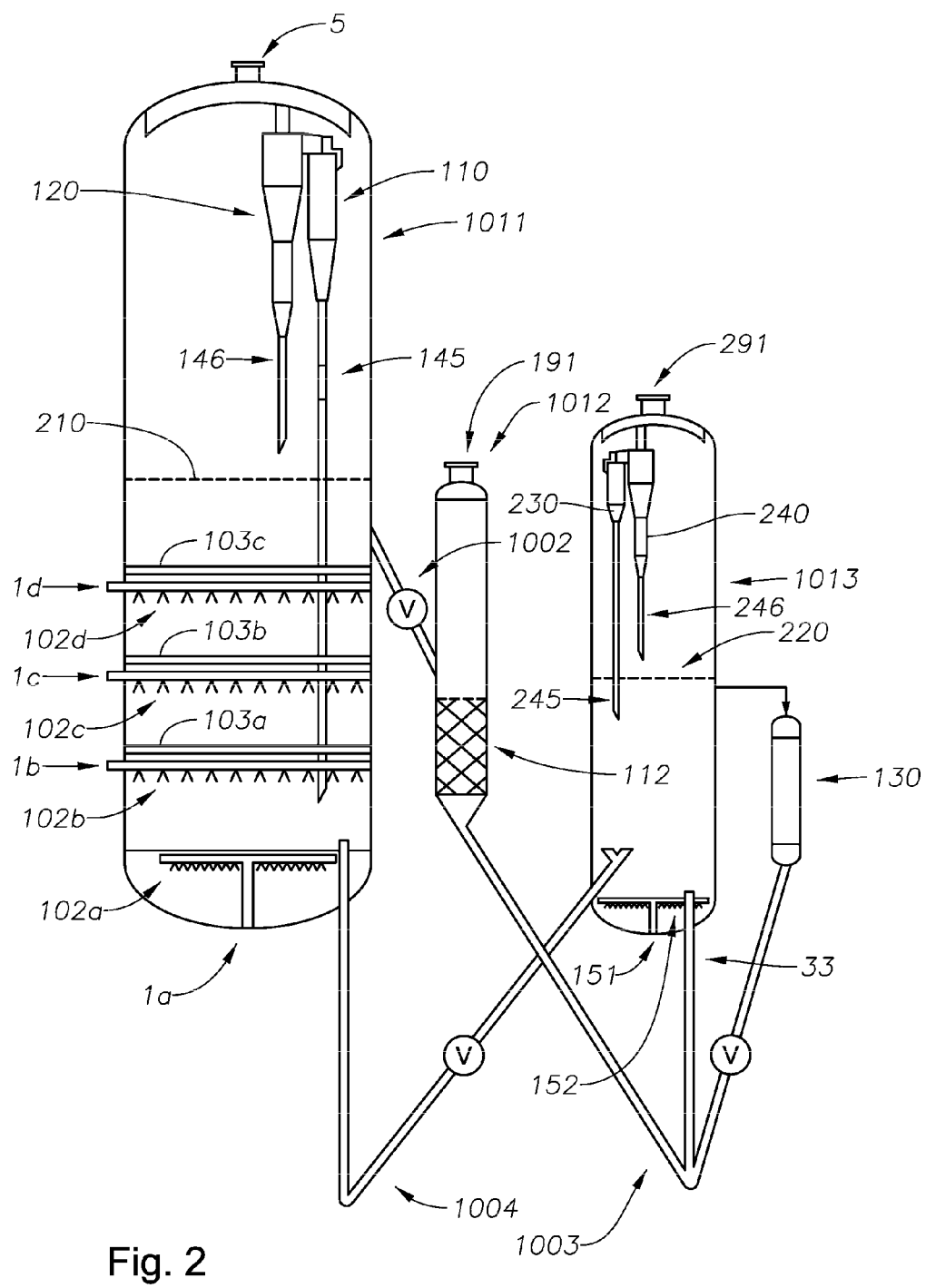
FIG. 2 is a schematic of a reactor system including reactor and regenerator and some associated auxiliary devices and transfer piping according to the present invention.

The present invention may be better understood by reference to a specific embodiment of the invention illustrated schematically by FIG. 2.

In FIG. 2, one or more reactants are provided in stages through plural conduits 1a-1d to feed plural spargers 102a-102d in the fluid bed reactor 1011. In embodiments the reactants may be sparged as a gas, as a liquid, or a combination thereof. In other embodiments, different reactants may be provided through different conduits, so that, by way of example, toluene and/or benzene may be provided through conduit 1a and methanol may be provided through each of plural conduits 1b, 1c, and 1d. In embodiments water and/or steam may also be provided through one or more of the plural conduits with one or more of the reactants. Conduit 1002 represents a transfer line to stripper 1012, with a valve illustrated symbolically by "V" here and elsewhere in the drawing; conduit 1003 transfer line to regenerator 1013; conduit 1004 is the transfer line to fluid bed reactor 1011; 5 is the fluid bed reactor 1011 effluent outlet (i.e., comprising desired product paraxylene); element 1012 represents the catalyst stripper apparatus, detailed features of which are per se known in the art and do not form a part of the present invention, except as otherwise explicitly set forth herein; element 1013 represents the fluid bed regenerator, detailed features of which are also per se known in the art and do not form a part of the present invention, except as otherwise explicitly set forth herein; conduit 33 is the riser transfer line to regenerator 1013. Element 291 is a vent for flue gases (e.g., $CO_2$, CO, $H_2O$, $N_2$, $O_2$).

Continuing with the description of FIG. 2, elements 102a-102d are plural, staged, spargers, which may be of the type known in the art; elements 103a-103c represent plural structure packing layers, described in more detail below.

Continuing again with FIG. 2, elements 110, 120, 230 and 240 represent cyclones which in certain embodiments are important features of the present invention and are described in more detail below. Element 110 is the secondary cyclone for fluid bed reactor 1011; 112 represents the dense bed for catalyst stripper 1002, 120 represents the primary cyclone for reactor 1011, and element 130 is the catalyst cooler, which is also per se known in the art, the detailed features of which do not form a part of the present invention, except as otherwise explicitly set forth herein. Additional features include 145, the secondary cyclone dipleg; 146, the primary cyclone dipleg; 151, the regenerator gas sparger (regenerator gas is, at the inlet, advantageously air or oxygen); 191, the stripper gas outlet; 210, illustration of preferred dense bed level in reactor 1011; 220, illustration of preferred dense bed level in the regenerator 1013; 230, the secondary cyclone for regenerator 1013; 240, the primary cyclone for regenerator 1013; 245, the regenerator secondary cyclone dipleg; and 246, the regenerator primary cyclone dipleg.

Cyclones per se are often used in fluid-solid systems. In the present system they are used for separation of the catalyst particles from the gas flow, so that the gas (either reactor effluent, or regenerator flue gas) can leave the vessel, and the catalyst can be returned back to the fluid bed. The gas-solids mixture would first go through the primary cyclone (120, 240), with the majority of the solids separated and returned to the fluid bed through the dipleg (146, 246). Then the gas flow with a much lower solids fraction goes through a secondary cyclone (110, 230), further separating the solids from the gas stream, returned to the fluid bed through the dipleg (145, 245).

Other means of separation of catalyst particles may be used instead of, or in addition to what is represented schematically in FIG. 2. By way of example, one or more quench towers, centrifuges, filters, settling tanks, and the like. Advantageously, one or more external cyclones may be used, in addition to the internal cyclones represented schematically in FIG. 2. Such external cyclones can be placed, for instance, upstream or downstream of the rector effluent heat exchange network (not shown in the drawings). One of skill in the art, in possession of the present disclosure could provide the appropriate engineering to integrate such additional apparatus.

It will be appreciated by one of ordinary skill in the art that additional valves, piping and other details of a functioning apparatus are not shown for convenience of view, and also that more or less than certain specific features may be used, such as additional stages of packing, of spargers, and the like, in reactor 1011, or that the levels of beds 210, 112, 220 may be different than specifically illustrated in FIG. 2. Likewise, exact number and positioning of cyclones and associated diplegs, entrance and exits positions of the various feeds transfer lines, valves, and the like may also be different than exactly shown in FIG. 2. Thus, it should be clear that the invention may be practiced otherwise than as specifically embodied herein, without departing from the scope of the disclosure and appended claims. Nevertheless, levels of the beds 210, 112, 220, and proportions of the various apparatus 1011, 1012, and 1013, as well as cyclones and diplegs 120, 110, 240, 230, 146, 145, 245, and 246, are as shown in FIG. 2.

It will further be appreciated by one of skill in the art in possession of the present disclosure that the plural structured packing material and plural staged injection may be accomplished by having plural reactors in series. In this regard, reference is made to FIG. 3, wherein FIG. 3a represents schematically a configuration analogous to FIG. 2, that is, with plural injection of, for instance, toluene and/or benzene through conduits 1001a, and methanol through conduits 1002a, 1002b, and 1002c. The structured packing is represented by elements 1103a, 1103b, and 1103c. In FIG. 3b, the injection staging provided by conduits 1001a, and 1002a, and then separately by 1002b in a separate reactor, connected in series by conduit 1005, with structured packing elements 1103a and 1103b provided in separate reactors. In these FIGS. 3a and 3b plural spargers and cyclones/diplegs, as well as the catalyst stripper and regenerator are not shown for convenience of view. The product effluent 5, a stream of xylene, is the common product in either arrangement. In an embodiment, the system shown in FIG. 3b can share a single catalyst stripper and/or regenerator.

Regarding structured packing, illustrated in FIG. 2 at plural staged positions 103a-103c in a single reactor, in FIG. 3a at plural staged positions 1103a-1103c in a single reactor, or in FIG. 3b at plural stages positions 1103a-1103b in reactors in series, numerous structured packing material is known in the art, such as those structured packings used in distillation columns. In preferred embodiments of the present invention, multiple layers of Koch-Glitsch™ KFBE™ IIB, such as 1-foot (30-31 cm) are particularly useful to separate the dense fluid bed into multiple stages. This type of packing has been found particularly useful for a fluid bed reactor for the alkylation of benzene and/or toluene using methanol as an alkylating agent and a catalyst comprising a molecular sieve, such as ZSM-5, because of its high open area for both gas and catalyst solids to pass through and its capability to control bubble sizes. When larger bubbles from a lower stage reach the staging baffles, gas is redistributed by the packing structure and form smaller bubbles into the next higher stage. While FIG. 2 illustrates specific proportions of the elements, each stage of structured packing 103a-103c (or 1103a-1103b in FIG. 3A or 1003a-1003b in FIG. 3B) may be, for instance, 5-35 cm thick, such as 5 cm, 10 cm, 18 cm, 27 cm, 30 cm, 31 cm, 35 cm, etc.) with each layer individually selected, or they may be of uniform thickness, or a mixture of uniform and non-uniform thickness, of structured packing of the type discussed above, wherein the whole dense bed (210 in FIG. 2; not shown in FIGS. 3A or 3B) has a height of from 300-1000 cm, such as about 350 cm, or 450 cm, or 600 cm, or 700 cm, or 900 cm). With this staged design according to the present invention, the maximum height for bubbles to grow can be reduced, minimizing the forming of large bubbles and gas by-pass. In a preferred embodiment, the toluene main sparger is located at the bottom of the first lower stage and three to five smaller spargers inject methanol into each of the dense bed stages. Each methanol sparger is located below a layer of packing for optimal distribution of methanol gas injected into the fluid bed.

It will be recognized by one of skill in the art that although spargers are specifically referred to herein, in general, numerous specific apparatus can be used to inject the reactants.

In another specific embodiment, the toluene injected at the bottom of the reactor has a separate sparger from the bottom level methanol injection, instead of a single sparger for the mixture of toluene and methanol. This separate sparger configuration provides flexibility in both apparatus construction and operation. For instance, a separate toluene sparger allows reduced water co-feed level for the toluene sparger to minimize the amount of inert steam fed into the reactor. Separating methanol from the toluene feeding lines also allows a higher feed temperature for toluene in order to provide more heat to maintain the reactor energy balance. In preferred embodiments, the methanol sparger(s) may be lined with refractory to reduce heat transfer from the hot fluid bed into the methanol in the sparger. This avoids methanol heating up to decomposition temperature prior to contacting toluene and catalyst.

Various numbers of methanol injection levels were tested using a fluid bed reactor having reactor dimensions within the bounds illustrated by reactor 11 in FIG. 2, and four methanol spargers were found to produce most of the benefit.

During experimental runs without structured packing, large bubbles were formed using catalyst particles having a small amount of fines. The bubbles were sometimes as large as the diameter of the 4 inch (about 10 cm) fluid bed and caused slugging. Significant decrease in methanol conversion and paraxylene selectivity in the performance data was correlated to such poor fluidization. This shows that it is beneficial to maintain smaller bubble sizes and uniform fluidization in the fluid bed reactor, as provided by the present invention.

In a separate cold flow study in a 3-ft diameter (about 91 cm) fluid bed, the same type of packing with the same thickness and height configuration was tested. Methanol and toluene spargers were also simulated in the same height and flow rate configurations. Data was obtained with and without the staging baffles. By using tracer techniques and high frequency pressure drop measurements, it was observed that the configuration with staging baffles was proven to greatly reduce gas phase back-mixing and gas by-pass. Using kinetic modeling studies of the type well-known in the art, it can be shown that selectivity to paraxylene can be increased from about 60-70 wt % to 80 wt % or above, such as 90 wt %, using a reactor and process according to the present invention, when compared to a reactor without the staged baffles.

In preferred embodiments, the configuration of a deep fluid bed with structure packing as staging baffles and staged methanol injection may be characterized by the following:
- a) structured packing (such as Koch-Glitsch™ KFBE™ IIB) layers in deep dense fluid bed as staging baffles to control bubble sizes, reduce gas phase back-mixing, and gas by-pass;
- b) staged methanol injection with multiple spargers, each under a layer of the staging baffles; and
- c) separate toluene and methanol spargers, with toluene sparged at the bottom of the reactor, and methanol sparged at plural stages upstream of the toluene spargers.

It is further beneficial to maintain methanol conversion at a constant level by adjusting the catalyst holdup, catalyst activity, or a combination of both. Catalyst holdup means the height of the reactor dense bed level (210 in FIG. 2), which can be altered up or down by varying the catalyst withdrawal rate. Catalyst activity can be controlled by several methods, including changing the weight hourly space velocity and/or catalyst regeneration conditions. It is beneficial to control these aspects of operation with a goal of decreasing fluctuations in methanol conversion, to keep constant reactor effluent composition to minimize the impact on downstream material separation and recycling as well as on the overall process productivity.

In embodiments there are three, four, five, six, etc., stages of methanol injection and the amount of methanol introduced at each stage is from 0-99 mol %, or 0-40 mol %, or from 0-33 mol %, based on the total amount of methanol injected. As described elsewhere herein, the system may also be operated with one or more or the plural injection stages and baffle stages in separate reactors in series. In a preferred embodiment, all stages operate with substantially similar amounts of methanol injection, e.g., three sparger stages each injecting between about 30-35 mol % of the total methanol injected, such as each about 33 mol %, or four sparger stages each injecting between about 20-30 mol %, such as each about 25 mol % of the total methanol injected. In this preferred embodiment it is still more preferred that in the case of upset that one or more of the sparger stages be modified within the range of 0-50 mol %, with the others modified accordingly. Typically the uppermost sparger stage (which could be the third, or fourth or fifth stage) would be adjusted within that range, or even shut down, so that the other three sparger stages (in the case of four total sparger stages) operated at about 33 mol % of the total methanol injected, until normal operating conditions can be re-established. In an alternative embodiment, there are at least two stages of methanol injection with each injection stage introducing at least 5 wt % of the total amount of all methanol injected at all injection stages. As a further alternative, there are at least three injection stages, with each stage introducing at least 10 wt % of all methanol injected at all injection stages. Numerous additional operating scenarios could be readily envisioned by one of ordinary skill in the art in possession of the present disclosure.

One or more catalysts that promotes the alkylation reaction may be used in the present invention. For example, ZSM-5 zeolite such as disclosed in WO 98/14415 or any of the prior art patents set forth in the Background section above, is suitable for the present invention. In certain embodiments a phosphorus-containing ZSM-5 zeolite that has been steam-treated is preferred. The catalyst also preferably comprises clay as a binder.

Suitable reaction conditions, particularly for methylation of toluene with methanol to produce para-xylene, may be readily determined by one of ordinary skill in the art in possession of the present disclosure. Such suitable reaction conditions may include the following ranges: (a) Temperature—about 500° to about 700° C., and preferably between about 500° to about 600° C.; (b) Pressure—about 1 atmosphere to about 1000 psig (about 100 to about 7000 kPa), and preferably about 10 psig to about 200 psig; (c) moles toluene/moles methanol (in the reactor charge)—at least about 0.2, and preferably from about 0.2 to about 20; and (d) a weight hourly space velocity ("WHSV") for total hydrocarbon feed to the reactor(s) of about 0.2 to about 1000, preferably about 0.5 to about 500 for the aromatic reactant, and about 0.01 to about 100 for the combined alkylating reagent stage flows, based on total catalyst in the reactor(s).

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. Trade names used herein are indicated by a ™ symbol or ® symbol, indicating that the names may be protected by certain trademark rights, e.g., they may be registered trademarks in various jurisdictions. When numerical lower limits and numerical upper limits are listed herein, ranges from any lower limit to any upper limit are contemplated.

The invention has been described above with reference to numerous embodiments and specific examples. Many variations will suggest themselves to those skilled in this art in light of the above detailed description. All such obvious variations are within the full intended scope of the appended claims.

What is claimed is:

1. In a fluid bed reactor system for the manufacture of xylene by an alkylation reaction comprising contact of an alkylating agent selected from methanol, dimethyl ether, and mixtures thereof with an aromatic hydrocarbon selected from benzene, toluene, and mixtures thereof, in the presence of a catalyst that promotes said alkylation reaction, the improvement comprising the staged injection of at least one of said alkylating agent and said aromatic hydrocarbon, wherein said reactor system is characterized by plural injection stages separated by baffle material, said baffle material characterized as suitable to decrease at least one of gas phase back-mixing, by-pass phenomena, and gas bubble size in the manufacture of xylene by said alkylation reaction but allow said catalyst to pass through said baffle material.

2. The fluid bed reactor system of claim 1, wherein said alkylating agent is introduced downstream of benzene and/or toluene by said staged injection.

3. The fluid bed reactor system of claim 1, wherein said catalyst is selective for the production of paraxylene relative to meta- and orthoxylene.

4. The fluid bed reactor system of claim 1, wherein said catalyst comprises ZSM-5.

5. The fluid bed reactor system of claim 1, wherein said catalyst comprises a phosphorus-containing molecular sieve that has been steam treated prior to said contacting.

6. The fluid bed reactor system of claim 1, wherein said baffle material is provided in at least two separate reactors in series, wherein each reactor has at least one zone comprising an injection stage for at least one of said reactants.

7. The fluid bed reactor system of claim 1, comprising a single reactor having plural injection stages and plural zones comprising baffle material.

8. The fluid bed reactor system of claim 1, further comprising at least one internal cyclone separator in said fluid bed reactor system.

9. The fluid bed reactor system of claim 1, wherein said baffle material comprises structured packing.

10. The fluid bed reactor system of claim 1, further comprising at least one external cyclone separator in said fluid bed reactor system.

\* \* \* \* \*